United States Patent
Ross et al.

(10) Patent No.: US 9,339,290 B2
(45) Date of Patent: *May 17, 2016

(54) ULTRASONIC SURGICAL INSTRUMENTS

(71) Applicant: COVIDIEN LP, Mansfield, MA (US)

(72) Inventors: Anthony B. Ross, Boulder, CO (US); Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Arlen K. Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/710,146

(22) Filed: May 12, 2015

(65) Prior Publication Data

US 2015/0238220 A1 Aug. 27, 2015

Related U.S. Application Data

(63) Continuation of application No. 13/435,922, filed on Mar. 30, 2012, now Pat. No. 9,028,515.

(60) Provisional application No. 61/469,549, filed on Mar. 30, 2011.

(51) Int. Cl.
*A61B 17/32* (2006.01)
*A61B 17/00* (2006.01)
(Continued)

(52) U.S. Cl.
CPC .............. *A61B 17/320092* (2013.01); *A61B 2017/00022* (2013.01); *A61B 2017/0084* (2013.01); *A61B 2017/00853* (2013.01); *A61B 2017/2829* (2013.01); *A61B 2017/2926* (2013.01)

(58) Field of Classification Search
CPC ............... A61B 17/320092; A61B 2017/0084; A61B 2017/2926; A61B 2017/2829; A61B 2017/00022; A61B 2017/00853
See application file for complete search history.

(56) References Cited

U.S. PATENT DOCUMENTS

| 5,389,098 A | 2/1995 | Tsuruta et al. |
| 5,534,346 A | 7/1996 | Robinson |

(Continued)

FOREIGN PATENT DOCUMENTS

| JP | 2000237204 A | 9/2000 |
| WO | 2006/042210 A2 | 4/2006 |
| WO | 2007143439 A2 | 12/2007 |

OTHER PUBLICATIONS

Bullock, P. et al., Haemostasis in Surgery, Jan. 2007, Imperial College Press, Chapter 2, p. 271.*

*Primary Examiner* — Ashley Fishback

(57) ABSTRACT

An ultrasonic surgical instrument is provided. The ultrasonic surgical instrument includes a housing having an elongated shaft extending therefrom. The shaft has a jaw member disposed at a distal end thereof. The jaw member is movable between an open configuration and a clamping configuration and includes a tissue contacting surface thereon. A cutting blade extends from a distal end of the shaft and operably couples to the housing and adjacent the jaw member to treat tissue. A selectively removable laminate liner is positionable over the tissue contacting surface of the jaw member and configured to prevent contact between the tissue contacting surface and the cutting blade when the cutting blade is treating tissue.

16 Claims, 3 Drawing Sheets

(51) Int. Cl.
*A61B 17/28* (2006.01)
*A61B 17/29* (2006.01)

(56) References Cited

U.S. PATENT DOCUMENTS

| | | |
|---|---|---|
| 5,582,611 A | 12/1996 | Tsuruta et al. |
| 5,849,022 A | 12/1998 | Sakashita et al. |
| 6,086,586 A | 7/2000 | Hooven |
| 6,129,735 A | 10/2000 | Okada et al. |
| 6,174,309 B1 | 1/2001 | Wrublewski et al. |
| 6,626,901 B1 | 9/2003 | Treat et al. |
| 6,786,905 B2 | 9/2004 | Swanson et al. |
| 6,860,880 B2 | 3/2005 | Treat et al. |
| 6,887,252 B1 | 5/2005 | Okada et al. |
| 7,329,257 B2 | 2/2008 | Kanehira et al. |
| 7,455,645 B2 | 11/2008 | Goldenberg |
| 7,544,200 B2 | 6/2009 | Houser |
| 9,028,515 B2 | 5/2015 | Ross et al. |
| 2003/0069571 A1 | 4/2003 | Treat et al. |
| 2003/0171747 A1 | 9/2003 | Kanehira et al. |
| 2004/0078035 A1 | 4/2004 | Kanehira et al. |
| 2009/0112200 A1 | 4/2009 | Eggers |
| 2010/0179545 A1* | 7/2010 | Twomey ............ A61B 18/1445 606/51 |

* cited by examiner

ULTRASONIC SURGICAL INSTRUMENTS

CROSS-REFERENCE TO RELATED APPLICATION

The present application is a continuation of U.S. patent application Ser. No. 13/435,922, filed on Mar. 30, 2012, which claims the benefit of and priority to U.S. Provisional Application No. 61/469,549 filed on Mar. 30, 2011, the contents of each these prior applications are incorporated by reference herein in their entirety.

BACKGROUND

1. Technical Field

The present disclosure relates to ultrasonic surgical instruments. More particularly, the present disclosure relates to ultrasonic surgical instruments including one or more laminate liner configurations to prevent wear of tissue contacting surfaces on jaw members of the ultrasonic surgical instrument.

2. Description of Related Art

Ultrasonic energy-powered instruments configured to cut and/or fragment tissue are known in the art. Ultrasonic instruments, typically, include a transducer that is coupled to a probe/waveguide having an active member (e.g., cutting blade, shear, hook, ball, etc.) at a distal end thereof. In use, ultrasonic energy is utilized to vibrate (e.g., at frequency usually in the range of 20 KHz to 60 KHz) the active member to treat tissue of interest.

Ultrasonic instruments may include any of a variety of probe configurations to achieve a specific surgical result. For example, the probe configuration may include an active member in the form of a cutting blade that is combined with a movable jaw configured to grasp and/or manipulate tissue. In certain instances, a tissue contacting surface (which is typically made from metal) of the movable jaw member may include a polytetrafluoroethylene (PTFE) liner configured to prevent the cutting blade from coming into contact with the tissue contacting surface. Such ultrasonic instruments are primarily used in a variety of medical procedures including open surgical procedures, luminal procedures, and endoscopic procedures.

During use, the movable jaw member provides support for tissue as the cutting blade vibrates to treat tissue. The PTFE liner and/or the tissue contacting surface of the movable jaw member may wear as a result of prolonged use. As can be appreciated, wear of the PTFE liner and/or the tissue contacting surface of the movable jaw member may result in a decreased surgical effect to tissue. That is, as the PTFE liner and/or tissue contacting surface wears, its tissue supporting capabilities may be diminished.

SUMMARY

In view of the foregoing, ultrasonic instruments including one or more laminate liner configurations to prevent wear of tissue contacting surfaces on jaw members of the ultrasonic surgical instrument may prove useful in the medical art.

Embodiments of the present disclosure are described in detail with reference to the drawings wherein like reference numerals identify similar or identical elements. As used herein, the term "distal" refers to a portion that is being described which is further from a user, while the term "proximal" refers to a portion that is being described which is closer to a user.

An aspect of the present disclosure provides an ultrasonic surgical instrument. The ultrasonic instrument includes a housing having an elongated shaft extending therefrom. The shaft includes a jaw member disposed at a distal end thereof. The jaw member is movable between an open configuration and a clamping configuration and includes a tissue contacting surface. A cutting blade extends from a distal end the shaft and operably couples to the housing adjacent to the jaw member to treat tissue. A selectively removable laminate liner is positionable over the tissue contacting surface of the jaw member and configured to prevent contact between the tissue contacting surface and the cutting blade when the cutting blade is treating tissue.

The selectively removable laminate liner may be provided on a spool that is operably coupled to the shaft. The laminate liner on the spool may be perforated into segments having a length approximately equal to a length of the tissue contacting surface of the jaw member.

The laminate liner may include one or more layers of lubricious material. The layer(s) of lubricious material may be polytetrafluoroethylene and/or silicone. The laminate liner may also include one or more layers of low-tack adhesive that is configured to removably couple the laminate liner to the tissue contacting surface. In some embodiments, the laminate is formed from a lubricious material having sufficient self-supporting strength, such as without limitation, PTFE tape.

A take-up spool may be operably coupled to the shaft and a slot adjacent the distal end thereof may be configured to receive the laminate liner therethrough for coupling the laminate liner to the take-up spool and provide a closed-loop configuration of laminate liner. The take-up spool may include a motor and may be in operable communication with a controller of a generator of the ultrasonic surgical instrument.

One or more sensors may be operably positioned on one of the jaw member or cutting blade. The sensors(s) may be configured to sense when the segment of laminate liner positioned on the tissue contacting surface of the jaw member is worn and communicates a signal to the controller to actuate the take-up spool to position a new segment of laminate liner over the tissue contacting surface.

An aspect of the present disclosure provides an ultrasonic surgical system. The ultrasonic surgical system includes an ultrasonic surgical instrument. The ultrasonic surgical instrument includes a housing having shaft extending therefrom. The shaft includes a jaw member disposed at a distal end thereof. The jaw member includes a tissue contacting surface. A cutting blade extends from a distal end of the shaft and operably couples to the housing adjacent to the jaw member to treat tissue. A spool of selectively removable laminate liners includes at least two layers of material and is positionable over the tissue contacting surface of the jaw member. The laminate liners configured to prevent contact between the tissue contacting surface and the cutting blade when the cutting blade is treating tissue.

The spool may be operably coupled to an interior surface of the shaft. The laminate liners on the spool may be perforated into segments having a length approximately equal to a length of the tissue contacting surface of the jaw member. The laminate liners may include one or more layers of lubricious material, e.g., polytetrafluoroethylene and/or silicone, and one or more layers of low-tack adhesive material configured to removably couple the laminate liner to the tissue contacting surface.

A take-up spool may be operably coupled to an interior surface of the shaft and a slot adjacent the distal end thereof may be configured to receive the laminate liners therethrough for coupling the laminate liners to the take-up spool and provide a closed-loop configuration of laminate liners. The take-up spool may include a drive unit, e.g., a motor and may be in operable communication with a controller of a generator of the ultrasonic surgical instrument.

One or more sensors may be operably positioned on one of the jaw member or cutting blade. The sensor(s) may be configured to sense when the segment of laminate liner positioned on the tissue contacting surface of the jaw member is worn and communicate a signal to the controller to actuate the take-up spool to position a new segment of laminate liner over the tissue contacting surface.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
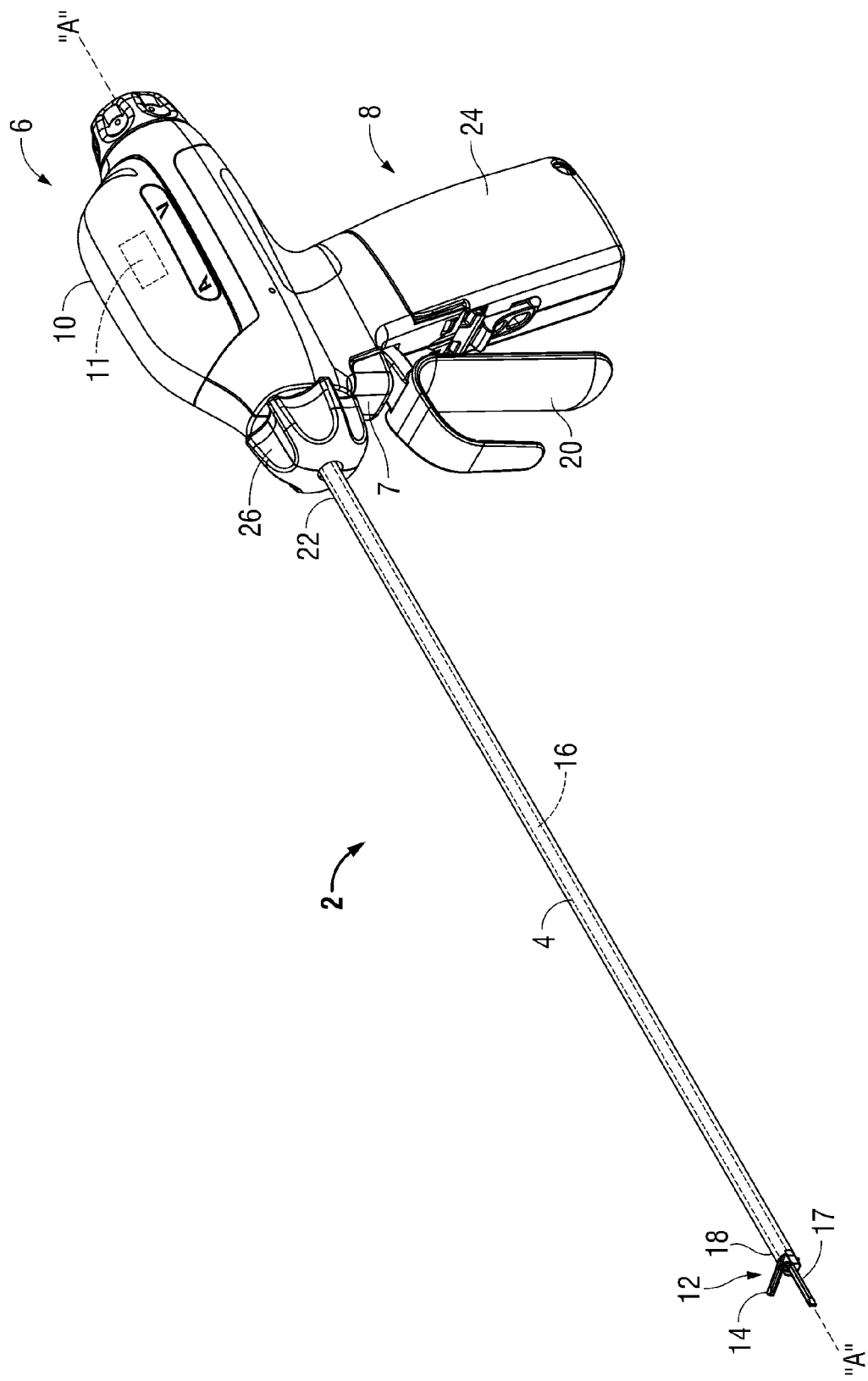
FIG. 1 is a right, perspective view of an ultrasonic instrument according to an embodiment of the present disclosure.

Turning now to FIG. 1, an ultrasonic surgical instrument 2 (instrument 2) according to an embodiment of the present disclosure is illustrated. In the illustrated embodiments, instrument 2 is described herein as being battery powered. Alternatively, instrument 2 may be externally powered, e.g., via a remote ultrasonic generator that couples to instrument 2. In the latter instance, a cable may couple instrument 2 to the generator.

Briefly, instrument 2 includes a housing 6 configured to house one or more components, e.g., transducer (not explicitly shown), a probe 16, and electrical circuitry that is configured for electrical communication with a battery assembly 8 of instrument 2. A proximal end of housing 6 is configured to releasably couple to an ultrasonic generator 10 and battery assembly 8. A distal end of housing 6 is configured to support and/or couple to a proximal end 22 of a shaft 4 having a longitudinal axis "A-A" defined therethrough. A rotation knob 26 operably couples to housing 6 and is configured to rotate shaft 4 approximately 360° in either direction about the longitudinal axis "A-A." Generator 10 includes the transducer that is coupled to probe 16 via a torque adapter (not explicitly shown) and configured to produce vibratory motion of a cutting blade 17 (FIGS. 1-2) disposed at a distal end of probe 16 when a trigger 7 is depressed. This vibratory motion of cutting blade 17 is utilized to treat tissue of interest. Battery assembly 8 includes a handpiece 24 having a battery (not explicitly shown) operably disposed therein.

Figure 2:
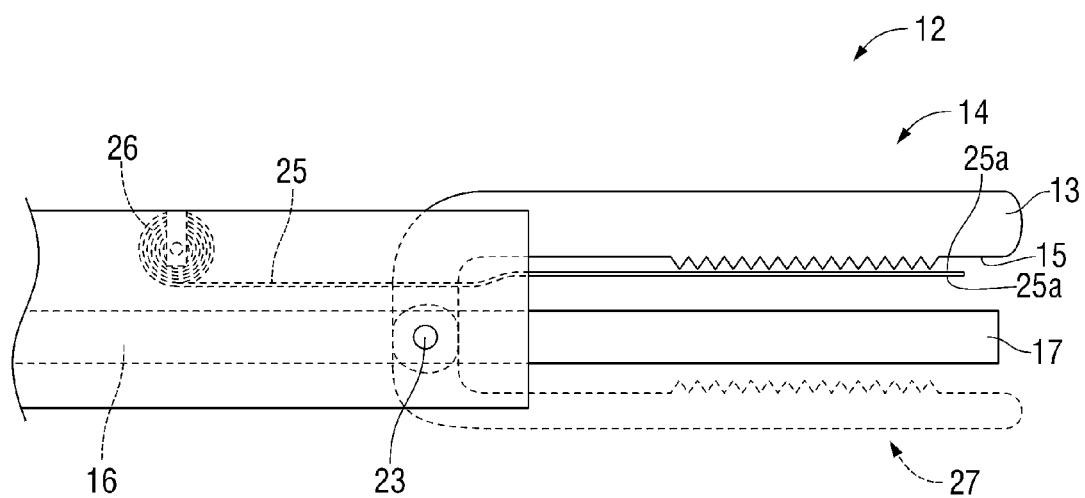
FIG. 2 is an enlarged, side, schematic view of a jaw member depicted in FIG. 1 configured for use with a laminate spool configuration according to an embodiment of the present disclosure.

With reference to FIGS. 1-2, an end effector 12 includes a first jaw member 14 (FIG. 1) that is supported at a distal end 18 of shaft 4 adjacent cutting blade 17. Jaw member 14 may be pivotably supported at the distal end of the shaft 4 via a pivot pin 23 and functions as a "clamping jaw." In particular, jaw member 14 is movable relative to cutting blade 17 (and/or the distal end 18 of the shaft 4) between an open configuration (FIG. 1) and a clamping configuration (FIG. 2) to clamp tissue when a lever or movable handle 20 (FIG. 1) is moved proximally. Jaw member 14 and cutting blade 17 are configured to collectively grasp and ultrasonically treat tissue. In particular, with tissue positioned between jaw member 14 and cutting blade 17, the cutting blade is configured to vibrate at a specific frequency (e.g., at a frequency in the range from about 20 KHz to about 60 KHz) to treat tissue.

Continuing with reference to FIG. 2, jaw member 14 is illustrated including a jaw housing 13 having a tissue contacting surface 15 operably coupled thereto. Tissue contacting surface 15 provides a compliant, temperature resistant and low friction surface for cutting blade 17 when the jaw member 14 is in the clamping configuration and cutting blade 17 is treating tissue, i.e., vibrating.

In the embodiment illustrated in FIGS. 1-4, tissue contacting surface 15 is provided with a selectively removable laminate liner 25 (liner 25) that is flexible (or compliant). In the illustrated embodiment, liner 25 includes one or more lubricious materials thereon, e.g., polytetrafluoroethylene, silicone, and the like.

Figure 3:
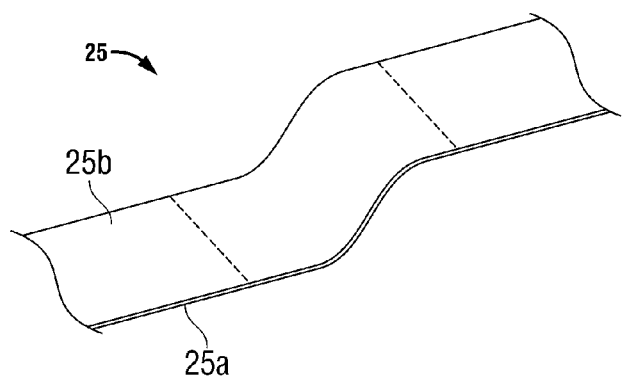
FIG. 3 is an enlarged, side, perspective view of a segment of laminate liner associated with the laminate spool configuration depicted in FIG. 2.

Continuing with reference to FIG. 3, liner 25 is illustrated including one or more layers of material. A first layer 25a includes the one or more lubricous material(s) thereon and is configured to contact cutting blade 17 when cutting blade 17 is treating tissue (FIG. 2). A second layer 25b is configured to releasably couple liner 25 to tissue contacting surface 15 (FIG. 2). To this end, second layer 25b may be provided with one or more low-tack adhesives thereon to facilitate releasably coupling liner 25 to tissue contacting surface 15. Alternatively, other methods may be utilized to releasably couple liner 25 to tissue contacting surface 15.

In accordance with the instant disclosure, liner 25 is provided on a spool 26 (FIG. 2) that is operably coupled to the shaft 4. In the illustrated embodiments, spool 26 is operably coupled to an interior surface of shaft 4 via one or more suitable coupling methods, e.g., a soldering, brazing, welding, via an integrally-formed mount, and the like.

In some embodiments, such as the illustrated embodiment, the liner 25 may be perforated into segments having a length approximately equal to a length of tissue contacting surface 15 of the jaw member 14, as best seen in FIG. 3. Providing a spool 26 of liners 25 that include perforations as described herein facilitates removing a worn segment of liner 25 to position a new segment liner 25. Alternatively, spool 26 may be provided with a single, non-perforated liner 25. The specific configuration of liner 25 may depend on a manufacturer's preference, a user's preference, and so forth.

In some embodiments, it may prove useful to provide a second jaw member 27 (shown in phantom in FIG. 2). In this particular embodiment, second jaw member 27 may include one or more laminate liners 25 (and operative components associated therewith) thereon configured to provide the same function as described above with respect to jaw member 14. Jaw member 27 may be configured similar to jaw member 14 to provide the same functions described herein. In the instance where two jaw members 14, 27 are utilized, The spool 26 may be configured to provide both jaw members 14, 27. Alternatively, a second spool (not explicitly shown) may be configured in a manner as described above with respect to spool 26 to provide jaw member 27 with liners 25, and a spool 26 may be configured provide jaw member 14 with liners 25. In some embodiments, spools 26 and/or 35 may be positioned externally relative to the shaft 4.

With reference again to FIGS. 1-2, cutting blade 17 is configured to treat tissue of interest and may be formed from any suitable material, including but not limited to metal, ceramic, or other suitable material. In the illustrated embodiments, cutting blade 17 may be formed from stainless steel or titanium. Metals of this type are suitable for forming bottom cutting blade 17 because of their ability to withstand high temperatures and vibrations that are, typically, associated with cutting blade 17 during operation thereof.

During use of one particular embodiment of the instrument 2, liner 25 is positioned over tissue contacting surface 15 and tissue may be positioned between jaw member 14 and cutting blade 17. Subsequently, trigger 7 may be depressed to activate cutting blade 17 to treat tissue of interest.

Under certain surgical scenarios, e.g., prolonged use of cutting blade 17, liner 25 may become worn due to excessive heat from cutting blade 17 or contact between cutting blade 17 and liner 25 as a result of cutting blade 17 severing tissue. In this instance, a user may pull the worn segment of liner 25 to position a new segment of liner 25 over tissue contacting surface 15. The worn segment of liner 25 may be torn at the perforation and discarded accordingly.

The unique configuration of instrument 2 including a spool 26 of liners 25 allows a user to change worn segments of liners 25 as needed. As a result thereof, the operative life of the jaw member 14, laminate liner 25 and/or cutting blade 17 is increased when compared to jaw members (and/or cutting blades) associated with conventional ultrasonic instruments.

From the foregoing and with reference to the various figure drawings, those skilled in the art will appreciate that certain modifications can also be made to the present disclosure without departing from the scope of the same. For example, in embodiments, one or more other methods may be utilized to provide tissue contacting surface 15 of jaw member 14 with a laminate liner 25.

Figure 4:
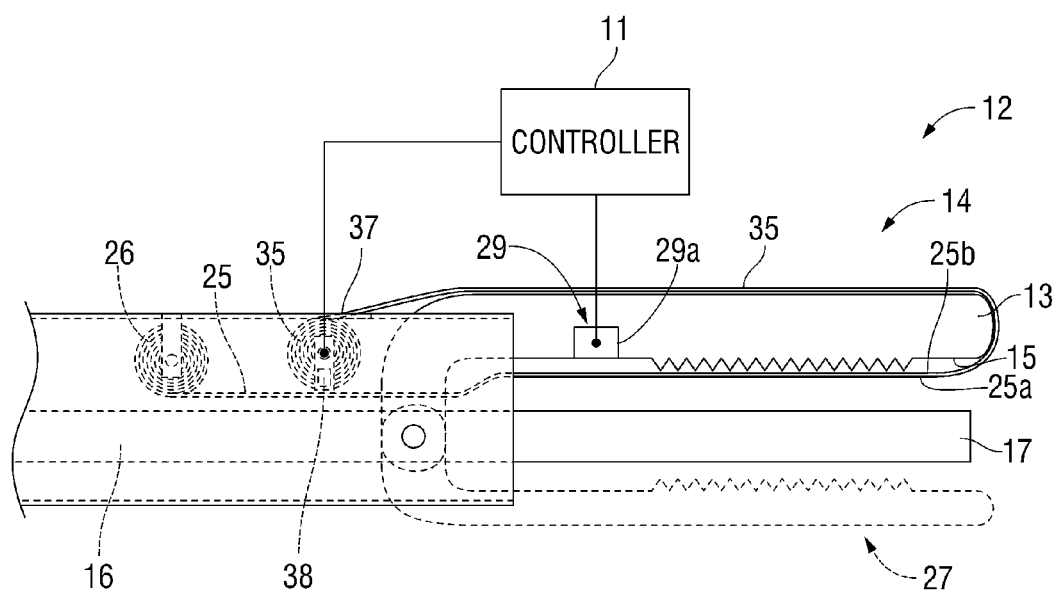
FIG. 4 is an enlarged, side, schematic view of the jaw member depicted in FIG. 1 configured for use with a laminate spool configuration according to another embodiment of the present disclosure.

With reference to FIG. 4, an alternate method of providing a new segment of liner 25 from spool 26 to tissue contacting surface 15 is illustrated.

In the embodiment illustrated in FIG. 4, a take-up spool 35 may be operably coupled to the interior surface of shaft 4 and configured to position a new segment of liner 25 from spool 26. In this particular embodiment, shaft 4 may include a slot 37 (FIG. 4) that is positioned adjacent distal end 18 of shaft 4. Slot 37 is configured to receive liner 25 therethrough for coupling liner 25 to take-up spool 35, and, thus provide a closed-loop configuration of liner 25. Take-up spool 35 is motor driven and includes a motor 38 (FIG. 4) that is in operable communication with a controller 11 (FIG. 1, for example) of generator 10, described in more detail below.

One or more sensors, 29 (FIG. 4) are operably positioned jaw member 14 or cutting blade 17. In the embodiment illustrated in FIG. 4, a sensor 29 is positioned on jaw member 14 adjacent tissue contacting surface 15. Sensor 29 is configured to sense when a segment of liner 25 positioned on tissue contacting surface 15 is worn. To this end, sensor 29 maybe any suitable type of sensor including, but not limited to temperature sensors, impedance sensors, pressure sensors and the like. In the illustrated embodiment, a temperature sensor is configured to sense a temperature of liner 25. In one particular embodiment, for example, when a temperature of liner 25 exceeds a predetermined threshold temperature, e.g., 200° C. or greater, temperature sensor 23 communicates a signal to the controller 11 to actuate motor 38 so that take-up spool 35 positions a predetermined length of a new segment liner 25 over tissue contacting surface 15. In embodiments, the predetermined length of a new segment liner 25 may be equal to the length of tissue contacting surface 15. In some embodiments, the predetermined threshold temperature may greater than, or lower than, 200° C., and may be user-selected and/or elected based upon a tissue parameter, an instrument parameter, the type of medical procedure being performed, the type of tissue of interest being treated, the type of liner in use, and so forth.

Additionally, or alternatively, sensor 23 may be configured to communicate a signal to the controller 11 when cutting blade 17 and tissue contacting surface 15 contact one another.

Control module 11 may be a component associated with generator 10 and/or battery assembly 8. In the illustrated embodiments, temperature control module 10 is provided as a component of the generator 10 (FIG. 1). Control module 11 may be configured to analyze the temperature data communicated thereto and utilize one or more control algorithms to control take-up spool 35. In one particular embodiment, instrument 2 and control module 11 may be configured to provide one or more indications, e.g., an audio indication "A", a visual indication "V", and so forth, to a user indicating that a new segment of liner 25 has been positioned over tissue contacting surface 15.

During use of one particular embodiment of the instrument 2, liner 25 is, initially, positioned over tissue contacting surface 15 and tissue may be positioned between jaw member 14 and cutting blade 17. Subsequently, trigger 7 may be depressed to activate the cutting blade 17 to treat tissue of interest.

Under certain surgical scenarios, e.g., prolonged use of cutting blade 17, liner 25 may become worn due to excessive heat from cutting blade 17 or contact between cutting blade 17 and liner 25 as a result of cutting blade 17 severing tissue. In the former instance, sensor 23 may communicate a signal to controller 11 as described above. Thereafter, controller 11 may actuate take-up spool 35 to position a predetermined length of a new segment liner 25 over tissue contacting surface 15.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   an elongate shaft;
   a cutting blade extending from a distal end of the elongate shaft;
   a jaw member disposed at a distal end of the elongate shaft and movable from a first position spaced-apart from the cutting blade to a second position closer to the cutting blade, the jaw member including a contact surface; and
   a movable liner positioned on the contact surface of the jaw member between the contact surface and the cutting blade, wherein the movable liner is operably coupled to the elongate shaft such that the movable liner is selectively movable relative to the contact surface of the jaw member.

2. The ultrasonic surgical instrument according to claim 1, wherein the movable liner is perforated into segments having a length approximately equal to a length of the contact surface of the jaw member.

3. The ultrasonic surgical instrument according to claim 1, wherein the movable liner includes at least one layer of lubricious material.

4. The ultrasonic surgical instrument according to claim 3, wherein the at least one layer of lubricious material is selected from the group consisting of polytetrafluoroethylene and silicone.

5. The ultrasonic surgical instrument according to claim 1, wherein the movable liner includes at least one layer of low-tack adhesive configured to couple the movable liner to the contact surface.

6. The ultrasonic surgical instrument according to claim 1, further comprising a spool on which the movable liner is provided.

7. The ultrasonic surgical instrument according to claim 1, further comprising a take-up spool operably coupled to the elongate shaft.

8. The ultrasonic surgical instrument according to claim 7, wherein the distal end of the elongate shaft further includes a slot configured to receive the movable liner therethrough for coupling the movable liner to the take-up spool and provide a closed-loop configuration of the movable liner.

9. The ultrasonic surgical instrument according to claim 8, wherein the take-up spool includes a motor.

10. The ultrasonic surgical instrument according to claim 9, wherein the motor is in operable communication with a controller of the ultrasonic surgical instrument.

11. The ultrasonic surgical instrument according to claim 10, further comprising at least one sensor operably positioned on one of the jaw member, the cutting blade, or the elongate shaft.

12. The ultrasonic surgical instrument according to claim 11, wherein the at least one sensor is configured to sense when a segment of the movable liner positioned on the contact surface of the jaw member is worn and communicate a signal to the controller to actuate the take-up spool to position a new segment of selectively removable liner on the contact surface.

13. The ultrasonic surgical instrument according to claim 11, wherein the take up spool is operably coupled to an interior surface of the elongate shaft.

14. The ultrasonic surgical instrument of claim 1, wherein the movable liner comprises at least two layers of material.

15. An ultrasonic surgical instrument, comprising:
an elongate shaft;
a cutting blade extending from a distal end of the elongate shaft;
a jaw member disposed at a distal end of the elongate shaft and movable from a first position spaced-apart from the cutting blade to a second position closer to the cutting blade, the jaw member including a contact surface; and
a movable liner configured for position on the contact surface of the jaw member between the contact surface and the cutting blade, wherein the movable liner is perforated into segments having a length approximately equal to a length of the contact surface of the jaw member.

16. An ultrasonic surgical instrument, comprising:
an elongate shaft;
a cutting blade extending from a distal end of the elongate shaft;
a jaw member disposed at distal end of the elongate shaft and movable from a first position spaced-apart from the cutting blade to a second position closer to the cutting blade, the jaw member including a contact surface; and
a movable liner configure for positioning on the contact surface of the jaw member between the contact surface and the cutting blade, wherein the movable liner includes at least one layer of lubricious material selected from the group consisting of polytetrafluoroethylene and silicone.

* * * * *